United States Patent [19]

Agris

[11] 3,994,301

[45] Nov. 30, 1976

[54] SUBMAMMARY DISSECTOR

[75] Inventor: Joseph Agris, Edison, N.J.

[73] Assignee: S & S Medical Products Co., Inc., Iselin, N.J.

[22] Filed: Apr. 14, 1975

[21] Appl. No.: 567,551

[52] U.S. Cl. .............................................. 128/305
[51] Int. Cl.² ........................................ A61B 17/32
[58] Field of Search ........................ 128/303 R, 305

[56] References Cited
UNITED STATES PATENTS

| 2,029,495 | 2/1936 | Lowe | 128/305 |
|---|---|---|---|
| 3,610,246 | 10/1971 | Salmon | 128/305 |
| 3,670,733 | 6/1972 | Carlisle | 128/305 |
| 3,740,779 | 6/1973 | Rubricuis | 128/305 X |

OTHER PUBLICATIONS

Leggiadro, "A Flexible Meniscotomy Knife", in Jour. Bone and Joint Surgery, 40–A[4]: 933–934, 1958.
Van Gorder et al., "The Central—Graft Operation for Fusion of Tuberculous Knees etc.", IN Jour. Bone and Joint Surg., 41–A[6]: 1029–1046, 1959.

Primary Examiner—Channing L. Pace
Attorney, Agent, or Firm—Friedman, Goodman & Teitelbaum

[57] ABSTRACT

A submammary dissector for providing a submammary pocket by insertion through an incision in a person's axilla the dissector having a curved portion at one end thereof and a handle portion at an opposite end thereof. A handle having a first grip is provided on the handle portion. The curved portion is provided with a rounded smooth tip and a dissecting notch. The upper surface of the curved portion and an intermediate portion of the dissector extending towards the handle portion are flat to provide a cleaving-like action which separates the breast at the level of the superficial fascia from the deep fascia of the underlying muscle. The undersurface of the dissecting instrument is round and smooth so that it may pass freely in the submammary space over the deep fascia of the pectoral muscle. Preferably, the curved portion is slightly tapered inwardly from the intermediate portion to the rounded tip. The handle portion is offset relative to the intermediate and curved portions for controlling movement of the curved portion. Additionally, the flat surface of the intermediate portion is provided with a scale to help determine the size and dimension of the dissected pocket, where the surgeon can easily and quickly determine distances of all portions of the dissected pocket allowing for accurate pocket formation.

8 Claims, 7 Drawing Figures

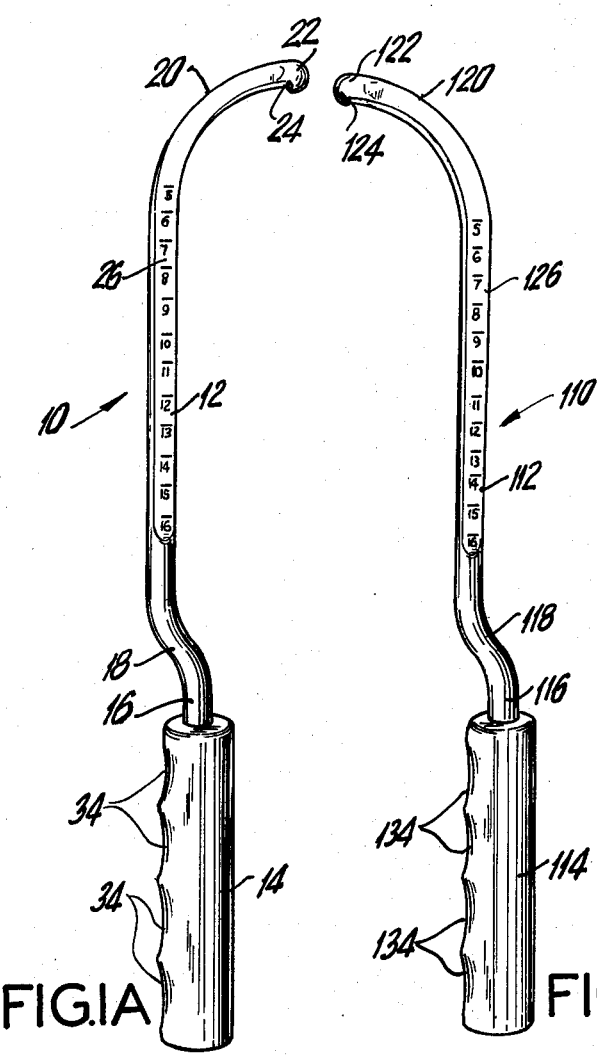
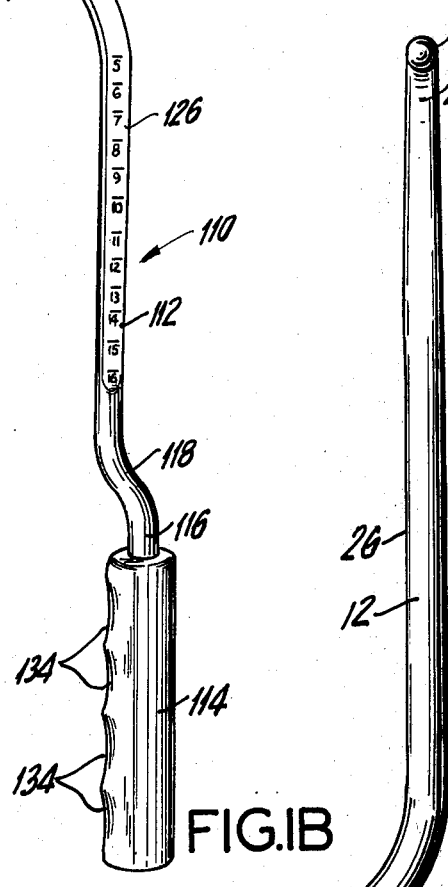
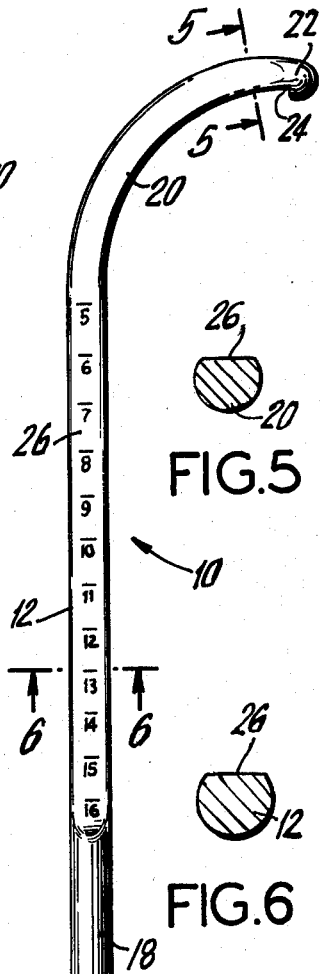
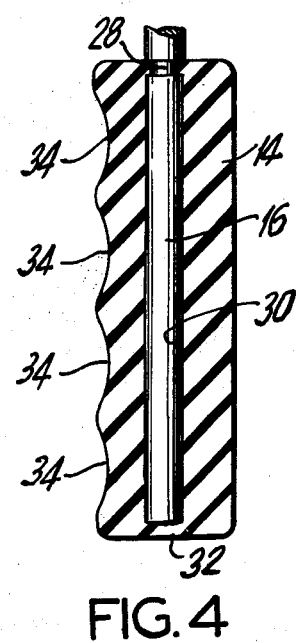
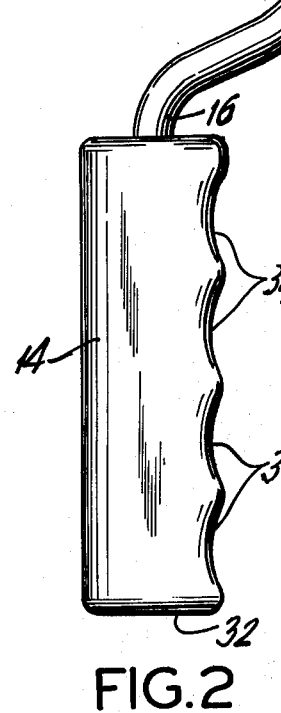
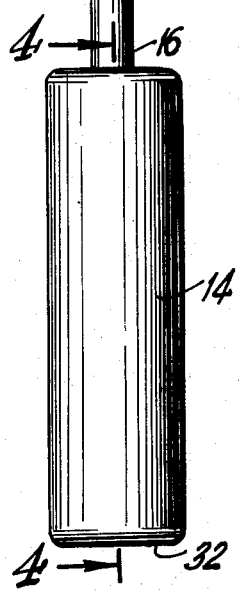
FIG.1A  FIG.1B  FIG.5  FIG.6  FIG.4  FIG.2  FIG.3

3,994,301

SUBMAMMARY DISSECTOR

BACKGROUND OF THE INVENTION

The present invention relates generally to a dissecting instrument, and more particularly to a submammary dissector for providing a submammary pocket by insertion through an incision in a person's axilla, where preferably a set of two submammary dissectors is employed, one dissector for insertion through a respective one of the person's armpits.

The present approach for augmentation mammaplasty to create an adequate submammary pocket, is for the surgeon to make an incision in the submammary area under the person's breast. The dissection is usually performed by the surgeon using sharp scissor dissection, then inserting his fingers into the incision and separating the breast from the underlying muscle with his fingers, forming an irregular pocket. After the submammary pocket has been formed by the surgeon, the prosthesis formed from a conventional filling material, is placed in the pocket and the incision is closed. The use of this procedure provides a pocket formation in which the prosthesis is in contact with the incisional scar, where the patient is left with a plainly visible scar in the breast area, where the length of the scar is approximately equal to the width of the pocket.

SUMMARY OF THE INVENTION

Accordingly, it is an object of the present invention to provide a submammary dissector for providing a submammary pocket in a person's breast which overcomes the disadvantages of the prior art.

It is another object of the present invention to provide a submammary dissector that can be inserted through an incision formed in a person's axilla to avoid visible scars by keeping the incision hidden high in the hairline of the axilla.

It is a further object of the present invention to provide a submammary dissector having a curved portion at one end thereof for separating the breast from the underlying muscle, and an offset handle portion at an opposite end thereof for controlling movement of the curved dissecting portion.

It is a still further object of the present invention to provide a submammary dissector as mentioned above having round and smooth undersurfaces to pass freely in the submammary space over the pectoral muscle, and having an upper flat surface to provide a cleaving-like action which separates the breast from the underlying muscle.

It is an added object of the present invention to provide a dissecting instrument as mentioned above having a scale on the flat surface to determine the size and dimension of the dissected pocket.

And yet another added object of the present invention is to provide a dissecting instrument that provides a rapid, simplified, and safe means of creating a submammary pocket, one which enables the surgeon to create an adequate pocket by way of the transaxillary approach in a simple, quick, and uncomplicated maneuver.

To this end, the present invention relates to a submammary dissector for providing a submammary pocket by insertion through an incision in a person's axilla, the dissector comprising a body member having an intermediate portion disposed between a curved portion at one end of the body member and a handle portion at an opposite end of the body member, the curved portion including dissecting means for separating the breast at the level of the superficial fascia from the deep fascia of the underlying muscle, the handle portion being offset relative to the intermediate and curved portions for controlling movement of the curved portion. The undersurfaces of the intermediate and curved portions are round and smooth to pass freely in the submammary space over the deep fascia of the pectoral muscle, while the upper portions are flat to provide a cleaving-like action which separates the breast from the underlying muscle functioning in conjunction with a dissecting notch formed in the curved portion adjacent to a rounded smooth tip to avoid laceration of the underlying muscle and fascia. Scale means are provided on the flat surface to help determine the size and dimension of the dissected pocket, where a handle with a fist grip is provided on the handle portion to permit a firm grasp of the instrument which provides strength, stability, balance and a tactile sensitivity during its use.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which:

FIGS. 1A and 1B illustrates perspective views of a set of submammary dissectors according to the present invention;

FIG. 2 illustrates a front elevational view of the dissector shown in FIG. 1A;

FIG. 3 illustrates a top plan view of the dissector of FIG. 2;

FIG. 4 illustrates a fragmentary cross sectional view taken along the line 4—4 in FIG. 3;

FIG. 5 illustrates an enlarged cross sectional view taken along the line 5—5 in FIG. 3; and FIG. 6 illustrates an enlarged cross sectional view taken along the line 6—6 in FIG. 3.

DETAILED DESCRIPTION OF THE PREFERRED EMBODIMENT

Referring now to the drawings, and more specifically to FIGS. 1A and 1B thereof, the present invention comprises a set of submammary dissectors generally denoted by the reference characters 10 and 110, respectively. The dissector 10 is used for one side of the patient's body, such as for insertion through the right armpit, and the dissector 110 is used for the other side, such as for insertion through the left armpit. Each of the dissectors 10, 110 includes a metal body member 12, 112 and a handle 14, 114 mounted on one end thereof. The handle 14, 114 are fabricated from plastic, hard rubber or any other suitable similar material. Each body member 12, 112 includes a handle end portion 16, 116 for receiving the respective handles 14, 114 as will be discussed hereinafter below.

The handle portions 16, 116 are offset from the remaining portion of the body member 12, 112 by offset portion 18, 118. The opposite end of each body member 12, 112 are arcuate to provide curved portions 20, 120. As shown in the drawings, the dissector 10 is similar to the dissector 110 except for the curvature of the portions 20, 120, where these portions 20, 120 curve in opposite directions for proper use thereof on each side of the patient's body. Accordingly, for simplification, the remaining FIGURES and discussion will be directed to dissector 10, however, it is understood that the following disclosure also relates to dissector 110.

As best shown in FIGS. 2 and 3, the curved portion 20 (120) is provided with a rounded smooth tip 22 (122) which allows for an adequate pocket contour without laceration of the underlying muscle and fascia. Adjacent to the tip 22 (122), the instrument is provided with a dissecting notch 24 (124) for separating the breast from the underlying muscle. The notch 24 is located on the inner curved surface of the curved portion 20 facing toward the handle 14. Accordingly, the offset portion 18 permits the surgeon when holding the handle 14 to better control the movement of the curved portion 20 and the notch 24 therein, especially when it is desired to pivot or rotate the tip 22.

As best shown in FIGS. 3, 5 and 6, the upper surface 26 (126) of the curved portion 20 (120) and intermediate portion of the body member 12 (112) is flat from the notch 24 (124) to the offset portion 18 (118) to provide a cleaving-like action which separates the breast from the underlying muscle in cooperation with the notch 24 (124). The undersurface of these flat portions extending from the surface 26 are round and smooth so that the instrument may pass freely in the submammary space over the deep fascia of the pectoral muscle.

By comparing the enlarged cross section shown in FIGS. 5 and 6, both enlarged the same degree, it is noted that the curved portion 20 (120) is tapered, decreasing in cross section from the intermediate portion to the tip 22, to provide easier insertion thereof into the incision and between the breast and underlying muscle. The curvature of the portion 20 is formed by a single radius to provide 90° of a circle from the intermediate straight portion to the notch 24, being approximately equal in circumference to one-half the size of a 220 to 240 centimeter prosthesis which is received in the dissected pocket. Accordingly, the longitudinal axis of the intermediate portion of the body member 26 is at right angles to a transverse axis passing through the tip 22.

The instrument is provided with a scale engraved in the flat surface 26, preferably in centimeters and one centimeter apart, being measured in a straight longitudinal direction from the outermost tip portion straight back towards the handle to define the depth thereof. The scale helps to determine the size and dimension of the dissected pocket, where the surgeon can easily and quickly determine the distances of all portions of the dissected pocket allowing for accurate pocket formation.

As shown in the drawings, the handle portion 16 and handle 14 thereon are offset directly above the flat surface 26, with the tip 22 being disposed to one side thereof, and the tip 122 being disposed to the opposite side of its respective handle 114. As shown in FIG. 4, a groove 28 is provided in the handle portion 16 to receive the open end of the handle 14 therein, which is formed by the longitudinally extending opening 30 provided in the handle 14. Preferably, the handle 14 is molded onto the handle portion 16 for securement therebetween, with the opposite end of the handle 14 being closed at 32. Additionally, the handle 14 (114) is provided with finger grooves 34 (134), to define a fist grip which permits a firm grasp of the instrument which provides strength, stability, balance and a tactile sensitivity during its use.

The instrument of the present invention provides a rapid, simplified, and safe means of creating a submammary pocket. The surgeon makes a small incision in the axillary, preferably hidden high in the hairline of the armpit to avoid any visible scars. This instrument is long enough to extend from the axilla along the submammary fascial cleft to create a pocket adequate for reception of the prosthesis. The configuration of the instrument allows for easy placement of the instrument into the axillary incision without interference of the arm and shoulder. The flat surface 26 within the person's body faces the front of the body with the tip 22 being directed towards the person's toes, being disposed between the breast and the underlying muscle. The use of this instrument permits pocket formation in which the prosthesis in no area is in contact with the incisional scar.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A submammary dissector for providing a submammary pocket by insertion through an incision in a person's axilla, said dissector comprising a body member having an intermediate portion disposed between an arcuate portion at one end of said body member and a handle portion at an opposite end of said body member, said arcuate portion including dissecting means for separating breast from underlying muscle, said arcuate portion having a free end fixedly located relative to said intermediate portion, said free end being provided with a rounded smooth tip to avoid laceration of underlying muscle and fascia, said arcuate portion having a curved surface facing towards said handle portion, said dissecting means including a notch disposed in said curved surface adjacent to said tip, said dissecting means further including a flat surface on one side of said arcuate portion, said flat surface extending from said tip to at least said intermediate portion for providing a cleaving-like action for separating the breast from the underlying muscle, an opposite side of said arcuate portion being round and smooth for a length equal to said flat surface for passing freely in submammary space over the deep fascia of the underlying muscle, said intermediate and arcuate portions lying along one plane with said handle portion being off-set in a perpendicular direction away from said flat surface to a second plane parallel to said one plane for controlling movement of said arcuate portion, said intermediate and handle portions extending along a longitudinal axis with said arcuate portion extending transversely to said longitudinal axis.

2. A submammary dissector as claimed in claim 1, wherein said intermediate portion is provided with scale means for determining size and dimension of the pocket.

3. A submammary dissector as claimed in claim 2, wherein said flat surface further extends along one side of said intermediate portion, said scale means being disposed on said flat surface of said intermediate portion.

4. A submammary dissector as claimed in claim 1, wherein a handle is disposed on said handle portion.

5. A submammary dissector as claimed in claim 4, wherein said handle is molded on said handle portion.

6. A submammary dissector as claimed in claim 4, wherein said handle is provided with fist grip means for permitting a firm grasp of said dissector which provides strength, stability, balance, and a tactile sensitivity during its use.

7. A submammary dissector as claimed in claim 1, wherein said arcuate portion tapers from a larger cross section adjacent said intermediate portion to a smaller cross section adjacent said tip.

8. A submammary dissector as claimed in claim 1, wherein said arcuate portion provides a 90° curvature from said intermediate portion to said tip.

* * * * *